United States Patent [19]
Woods et al.

[11] Patent Number: 5,633,411
[45] Date of Patent: May 27, 1997

[54] METHOD FOR PRODUCTION OF ALLYLOXYSTYRENE COMPOUNDS

[75] Inventors: John G. Woods, Farmington; Maria Masterson, Cromwell, both of Conn.

[73] Assignee: Loctite Corporation, Hartford, Conn.

[21] Appl. No.: 654,404

[22] Filed: May 28, 1996

Related U.S. Application Data

[63] Continuation-in-part of Ser. No. 482,441, Jun. 7, 1995, abandoned.

[51] Int. Cl.$^6$ .......................... C07C 41/00; C07C 43/02
[52] U.S. Cl. .......................... 568/654; 568/630; 568/657; 568/780; 568/790; 568/793; 568/804; 526/313; 528/86
[58] Field of Search .................... 568/630, 654, 568/657, 780, 790, 793, 804; 526/313; 528/86

[56] References Cited

U.S. PATENT DOCUMENTS

| | | | |
|---|---|---|---|
| 4,543,397 | 9/1985 | Woods et al. | 525/455 |
| 4,732,956 | 3/1988 | Woods et al. | 526/260 |
| 5,070,117 | 12/1991 | Klemarczyk et al. | 522/31 |
| 5,084,490 | 1/1992 | McArdle et al. | 522/181 |
| 5,087,772 | 2/1992 | Sheehan et al. | 568/804 |
| 5,141,970 | 8/1992 | McArdle et al. | 522/170 |

OTHER PUBLICATIONS

Crivello, et al, "Synthesis and Characterization of Bis(Isopropenylphenoxy) Alkanes and Bis(vinylphenoxy) Alkanes; Two Classes of Highly Reactive, Photopolymerizable Monomers," *J.M.S.—Pure Appl. Chem.*, A 29(9), pp. 753–754 (1992).

*Primary Examiner*—Samuel A. Acquah
*Attorney, Agent, or Firm*—Vidas Arrett & Steinkraus P.A.

[57] ABSTRACT

Allylic styrene ether compounds of the formula:

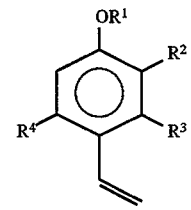

where $R^1$ is an optionally substituted allylic or propargyl hydrocarbon group, and $R^2$, $R^3$, and $R^4$ are independently H, $C_{1-6}$ hydrocarbon or $C_{1-6}$ hydrocarbonoxy groups, are prepared in a single pot reaction from relatively low cost materials. The method includes the steps of reacting a 4-acyloxystyrene of the formula

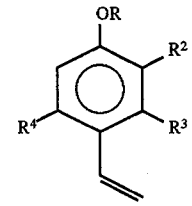

where R is an acyl group, with at least one mole of a base which can readily saponify or hydrolyze the phenolic ester bond per mole of acyloxystyrene, and then adding to the reaction mixture an alloylating agent of the formula $R^1X$, where $R^1$ is as previously defined and X is chloride, bromide, iodide, a sulfonic ester or a hydrocarbon sulfate group, to form said allylic styrene ether compound. The method may be employed to prepare mono-styryl functional compounds or di-styryl functional compounds such as 1,4-bis(4'-vinylphenoxy)but-2-ene.

27 Claims, No Drawings

METHOD FOR PRODUCTION OF ALLYLOXYSTYRENE COMPOUNDS

This application is a continuation-in-part of application Ser. No. 482,441, filed Jun. 7, 1995, now abandoned.

BACKGROUND OF THE INVENTION

4-Allyloxystyrene and compositions derived from this monomer are known and are disclosed as particularly useful for the production of photocured polymers and thermally resistant adhesives in McArdle et al, U.S. Pat. No. 5,084,490, (1992) and McArdle et al, U.S. Pat. No. 5,141,970, (1992). 4-Allyloxystyrene and related materials have also previously been found to be useful for the production of cationically polymerizable telechelic polymers as reported in Woods, et al, U.S. Pat. No. 4,543,397, (1985), and Woods et al, U.S. Pat. No. 4,732,956, (1988). In all of these cases, the 4-allyloxystyrene monomer was prepared in two separate stages involving firstly the conversion of 4-hydroxybenzaldehyde to 4-allyloxybenzaldehyde, by alkylation of the phenol with allyl bromide. In the second stage, the 4-allyloxybenzaldehyde was converted to 4-allyloxystyrene in a Wittig Reaction utilizing methyltriphenylphosphonium bromide. In all cases it was found to be necessary to isolate and purify the intermediate 4-allyloxybenzaldehyde by vacuum distillation prior to proceeding to the Wittig reaction stage. The synthesis of 4-allyloxystyrene by the Wittig route is outlined in Scheme 1.

Scheme 1. Two stage synthesis of 4-allyloxystyrene by Wittig route

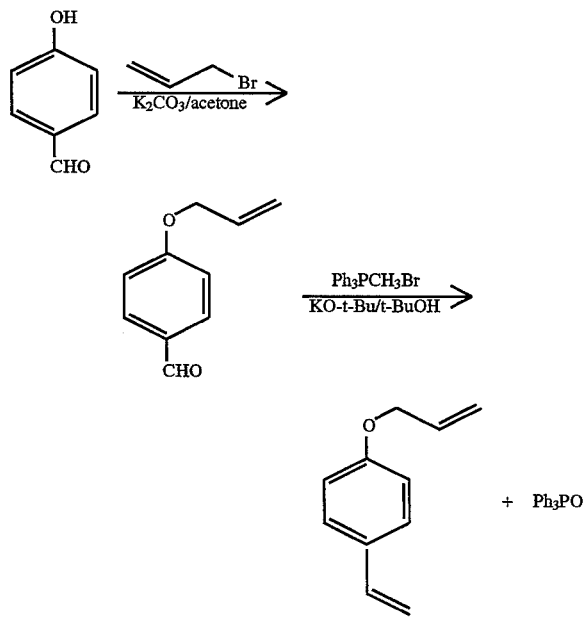

4-Allyloxystyrene is also a useful diluent in other cationically polymerizable systems, particularly those based on vinyl ethers such as disclosed in Klemarczyk et al, U.S. Pat. No. 5,070,117, (1991), and references cited therein.

Despite the many advantages of compositions derived from 4-allyloxystyrene, it has not been possible to develop commercial products based on these materials due to the high costs associated with the above synthetic methodology. In the first stage, the starting reagents, 4-hydroxybenzaldehyde and methyltriphenylphosphonium bromide, are needed in stoichiometric quantities and are costly materials. In the second stage, the Wittig reaction is particularly difficult and time consuming in relation to the removal of the unwanted byproduct, triphenylphosphine oxide. This material is the major product of the Wittig reaction and accounts for 63% of the crude product weight. The phosphine oxide is very soluble in 4-allyloxystyrene and separation requires careful precipitation of the oxide with large amounts of petroleum ether to reduce the concentration to a sufficient level to permit vacuum fractionation to be successful. Large-scale production of allyloxystyrene by this method is therefore costly by comparison to the production of other reactive monomers such as acrylates, epoxies or vinyl ethers.

The synthesis of the unalkylated monomer, 4-hydroxystyrene from 4-acetosystyrene is reported in Sheehan et al, U.S. Pat. No. 5,087,772, (1992). This reference states that aqueous saponification of 4-acetoxystyrene with potassium hydroxide results in the polymerization of the monomer and that a catalytic amount of base, such as potassium hydroxide at a concentration of 0.5–3.0 mole %, is critical in order to prevent the polymerization of the acetoxystyrene. The reaction of this reference is performed in the presence of excess alcohol and the acetic acid is removed in the form of the corresponding acetate.

Crivello, et al, J.M.S.—*Pure Appl. Chem.*, A29(9), pp 753–774 (1992), describes syntheses of isopropenylphenyl ether compounds by the condensation of 4-acetoxystyrene or 4-isopropenylphenyl acetate with α, ω-dihaloalkanes, or 2-chloroethyl vinyl ether in the presence of base.

SUMMARY OF THE INVENTION

The present development relates to a new synthetic process for the synthesis of allylic styrene ether compounds of the formula:

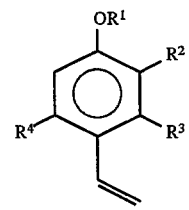

where $R^1$ is an optionally substituted allylic or propargyl hydrocarbon group, and $R^2$, $R^3$, and $R^4$ are independently H, $C_{1-6}$ hydrocarbon or $C_{1-6}$ hydrocarbonoxy groups, in a single pot reaction from relatively low cost materials. Specifically, 4-acyloxystyrenes can be converted to the desired 4-allyloxystyrene by treatment of the 4-acyloxystyrene with at least one, equivalent of a suitable base followed by about one equivalent of an alkylating agent of the formula $R_1X$ where $R^1$ is as previously defined and X is Cl, Br, I, a sulfonic ester group, or a hydrocarbon sulfate group.

In a preferred example, the commercially available 4-acetoxystyrene, can be converted to 4-allyloxystyrene in high yield (>80%) by reacting 4-acetoxystyrene with 2 equivalents of potassium hydroxide (i.e. 200 mole %), followed by 1 equivalent of allyl bromide. The by-products are readily removed by aqueous extraction and the product purified by vacuum distillation. That 4-allyloxystyrene could be prepared in this manner is surprising in view of Sheehan et al, U.S. Pat. No. 5,087,772, (1992) which states that aqueous saponification of 4-acetoxystyrene with potassium hydroxide results in the polymerization of the monomer and that a low catalytic amount of base, such as potassium hydroxide at a concentration of 0.5–3.0 mole %, is critical in order to prevent the polymerization of the acetoxystyrene.

The reactions are run in a solvent system. Solvent systems employing ethers having boiling points of from about 40° C. to about 130° C., with water dissolved therein at a level of about 5% or more, have been found to provide particularly beneficial scale up properties for the reactions.

DETAILED DESCRIPTION OF THE INVENTION

The new synthetic route is outlined in Scheme 2.

Scheme 2

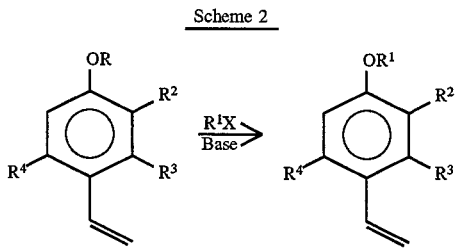

where R is an acyl group and $R^1$, $R^2$, $R^3$, $R^4$ and X are as previously defined.

In the formulae of Scheme 2, R may be any acyl group. In particular, R may be an aromatic acyl group, such as benzoate, and toluate, or an alkyl acyl group, such as acetate, propionate, butyrate, laurate, trimethylacetate or isobutyrate. The acyl group R may also be optionally substituted with halogen, or alkoxy groups. For instance, R may be trifluoroacetate, trichloroacetate, methoxybenzoate chlorobenzoate, etc. However, as R merely functions as a leaving group the most conveniently available acyl group is recommended, which is usually acetate. Acetate is also preferred because the alkali acetate byproduct can easily be removed by washing the reaction product with water.

The base employed in the reaction is one which can readily saponify or hydrolyze the phenolic ester bond. Generally alkali hydroxides, alkali metal alkoxides, and alkali metal hydrocarbon bases are suitable for this purpose. Alkali hydroxides are preferred as they are effective, cheap, and because water is generally a preferred component of the reaction mixture. Specific examples of suitable bases are lithium hydroxide, lithium methoxide, lithium ethoxide, n-butyl lithium, potassium hydroxide, potassium methoxide, potassium ethoxide, sodium hydroxide, sodium methoxide and sodium ethoxide.

The level of base should be at least one equivalent per equivalent of 4-acyloxystyrene compound employed in the reaction. Yields are significantly improved as the level of base is raised up to about 2 equivalents of base per equivalent of acyloxystyrene. For this reason the minimum level of base employed in the inventive method is preferably 1.5 equivalents, and more preferably at least 1.75 equivalents, of base per equivalent of acyloxystyrene. Optimal yields are obtained when the level of base is about 2 equivalents of base per equivalent of acyloxystyrene. Levels of base above about 2 equivalents per equivalent of acyloxystyrene may be employed but levels above about 2.1 equivalents per equivalent of acyloxystyrene are not recommended as such higher levels are ineffective for improving yield and the additional base is therefore merely unnecessary waste.

$R^1$ is an optionally substituted allylic or propargyl hydrocarbon group. Substitution may occur at any of the three carbon atoms of the allyl or propargyl group. Suitable substituents include alkyl, aryl, non-benzylic halo, or hydrocarbonoxy groups, for instance methyl, ethyl, phenyl, tolyl, chloro, bromo and methoxy.

X may be a chloro, bromo or iodo group. Of these, the order of reactivity is chloro<bromo<iodo. Fluoro groups are too inactive to be useful in the inventive method. When X is Br or Cl the rate of reaction can frequently be improved by adding a catalytic amount of an ionic iodide compound, such as a few crystals of potassium iodide, to the reaction mixture. X may also be a sulfonic ester group such as tolylate or triflate or a hydrocarbon sulfate group, in particular an alkyl sulfate such as a methyl sulfate or ethyl sulfate. Specific examples of suitable compounds $R^1X$ include, without limitation, allyl chloride, allyl bromide, allyl iodide, methallyl chloride, methallyl bromide, methallyl iodide, 3-chloro-1-butene, crotyl chloride, crotyl bromide, crotyl iodide, propargyl chloride, propargyl bromide, propargyl iodide, cinnamyl chloride, cinnamyl bromide, cinnamyl iodide, 3-phenyl-3-bromo-1-propene, 2-phenyl-3-bromo-1-propene, allyl methyl sulfate, methallyl methyl sulfate, allyl rosylate, methallyl tosylate, crotyl tosylate, cinnamyl tosylate and allyl triflate.

In the case where a non-allylic, non-benzylic, halo group is present on $R^1$, the alkylation reaction using $R^1X$ will generally not be substantially adversely affected because the allylic site of halogen X is much more reactive in the alkylation reaction than non-allylic, non-benzylic, halogen groups. However, it should be noted that the invention is intended to also encompass the use of compounds $R^1X$ in which there are actually two allylic chloride, bromide, iodide, sulfonic ester or sulfate groups per molecule, for instance 1,4-dibromo-2-butene. Such compounds can be considered to contain 2 equivalents X per molecule and can react at both allylic sites to provide an allyl ether which is difunctional with respect to 4-vinylphenoxy groups. Using 1,4-dibromo-2-butene as an example, the synthesis of such difunctional compounds is illustrated by Scheme 3 where Ac is an acetate group.

Scheme 3

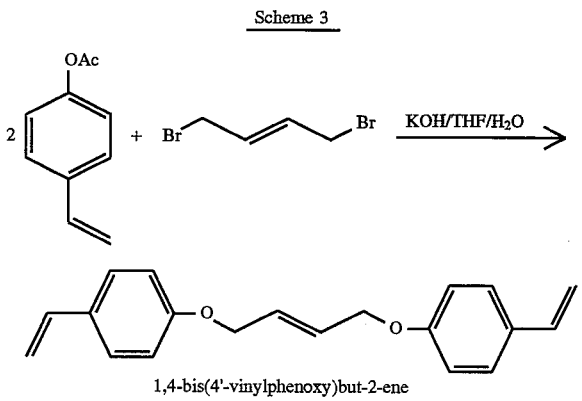

1,4-bis(4'-vinylphenoxy)but-2-ene

The groups $R^2$, $R^3$ and $R^4$ are preferably H. However, one or more of $R^2$, $R^3$ and $R^4$ may be $C_{1-6}$ hydrocarbon or hydrocarbonoxy, if desired. Suitable groups $R^2$, $R^3$ and $R^4$, other than H, include alkyl, alkenyl and alkoxy, for instance, methyl, ethyl, vinyl, methoxy and ethoxy.

The reaction is suitably run in a solvent to facilitate control of the reaction and to solrate the base. A solvent system which is capable of solubilizing the reactants and which does not take part in competing reactions with the reactants can be employed. Preferably the solvent system is an easily volatilized aprotic organic solvent in which water can be dissolved, or is a mixture of such a solvent and water. The solvent should also be one which allows scale up of the synthesis procedure without requiring that massive volumes of solvent be recycled or disposed of. Desirably, the solvent should also have relatively low toxicity and low odor. For this purpose linear or cyclic aliphatic ether solvents having a boiling point between about 40° C. and about 130° C., preferably from about 50° to about 120° C., in which water is soluble at a level of at least 5% by weight of the ether solvent, are particularily useful. Solvent systems based on mixtures of such solvents with 5–25% by weight water allow the reactants to be used at surprisingly high concentrations and therefore are very useful in commercial scale up. For scale up purposes it is desireable that the product be obtainable in high yield with an initial concentration of 4-acetoxystyrene of at least 1 mole per liter of the solvent system. Suitable examples of useful ether solvents include 1,4-dioxane (bp 100°–102° C.), 1,3-dioxane (bp 105°–106° C.), tetrahydrofuran (THF, bp 65°–66° C.), dimethoxymethane (bp 41°–42° C.), diethoxymethane (bp 87°–88° C.), 1,1-dimethoxyethane (bp 64° C.), 1,1-diethoxyethane (bp 102° C.), 1,2-dimethhoxyethane (ethylene glycol dimethyl ether, bp 85° C.), 1,2-dimethoxyethane (ethylene glycol diethyl ether, bp 121 ° C.) and tetrahydropyran (bp 88° C.). Of these, tetrahydrofuran is most preferred. Other solvents may also be used but may not afford the scale-up benefits of the ether solvents listed. Ester solvents are generally not suitable because they may saponify under the conditions employed. A preferred embodiment of the invention is employed for preparation of 4-allyloxystyrene from 4-acetoxystyrene, a commercially available compound, using allyl bromide and potassium hydroxide in a tetrahydrofuran/water solvent system. This reaction is represented in Scheme 4 below:

Scheme 4

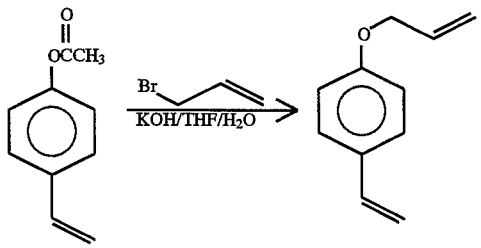

The reaction is believed to proceed through the intermediate formation of the potassium 4-vinylphenoxide salt which is then alkylated by allyl bromide with displacement of potassium chloride. The yield of product is maximized by the use of 2 equivalents of base, which it is believed, suppresses the formation of 4-vinylphenol by the exchange reaction of the phenoxide salt and acetic acid (acetic acid is a saponification product when less than 2 equivalents of base are employed).

The yield of the monomer is enhanced by the use of a small excess (approximately 10%) of allyl bromide and by the inclusion of a small amount of water in the reaction mixture. This latter measure improves the solubility of KOH in the reaction mixture. It is important to control the reaction exotherm following the addition of reagents. Generally it has been found that the slow addition of the reagents to the stirred reaction mixture, maintained at a temperature of about 5°–23° C. provides a mixture that may subsequently be controlled by means of an ice-bath.

The 4-allyloxystyrene, prepared by this method usually contains a small amount of 4-vinylphenol as a side product and may also contain some unreacted 4-acetoxystyrene. The presence of these materials does not detract from the thermal properties of the cured compositions containing the 4-allyloxystyrene. It is likely that the side-products copolymerize with the main monomers during the curing reaction. Nevertheless, the 4-vinylphenol may be removed almost completely by introducing a caustic extraction step during the reaction work-up. It is also expected that the concentration of 4-acetoxystyrene would be reduced by increasing the reaction time.

The invention is illustrated by the following non-limiting examples.

EXAMPLE 1

To a 4-necked, nitrogen swept, 2 liter glass reaction vessel equipped with a mechanical stirrer, double-walled condenser, thermometer and pressure compensating addition funnel was added tetrahydrofuran (THF) (600 mls), potassium hydroxide (143.4 g, 2.56 moles) and water (50 g). The mixture was stirred and cooled to 10° C. by means of an external ice-bath. 4-acetoxystyrene (207.4 g, 1.28 moles) was added over a 5 minute period and the solution was stirred for a further 1 hour while maintaining the temperature at 10° C. A solution of allylbromide (170.61 g, 1.41 moles) in THF (100 mls) was added dropwise over 15 minutes and the reaction mixture stirred for a further 1.5 hours, throughout which time the temperature was maintained at 10° C. The ice-bath was removed and the reaction mixture slowly heated by means of a heating mantle, to approximately 30° C., at which temperature a reaction exotherm occurred. As soon as the exotherm was observed, the heating mantle was replaced with an icebath to control the solvent reflux. During this time the reaction temperature increased to approximately 70° C. and the mixture refluxed vigorously. After the temperature had dropped to 50° C., the ice bath was removed and the mixture heated to 60° C. for 2.5 hours. After cooling to ambient temperature, the mixture was filtered and the solvent removed from the filtrate under reduced pressure. The residue obtained was dissolved in toluene (400 mls) and the solution washed with 2×400 ml portions of water. The organic solution was dried over sodium sulfate, filtered and the solvent removed under reduced pressure to yield a light yellow colored liquid (199 g). The liquid was distilled under vacuum to give a colorless liquid (b.p. 64°–67° C. at 0.2 mm of Hg) (172 g, 84%), which was identified as 4-allyloxystyrene from 1H nmr and IR analysis. Gas chromatographic analysis indicated a main product purity of 91% with small amounts of unreacted 4-acetoxystyrene (4%) and 4-vinylphenol (3%). The structure of the side products were continued by GC-mass spectral analysis.

EXAMPLE 2

The reaction described in Example 1 was repeated on the same scale but with the reaction temperature maintained in the range of 4°–6° C., rather than 10° C., during the addition of 4-acetoxystyrene and allyl bromide. In this case, 4-allyloxystyrene was obtained in 82% yield following vacuum distillation. Residual concentrations of 4-acetoxystyrene and 4-vinylphenol were 4 and 9% respectively.

EXAMPLE 3

The reaction described in Example 2 was repeated on 0.04 scale but with the reaction time decreased to 1 hour following the reaction exotherm. In this case, 4-allyloxystyrene was obtained in 88% crude yield.

EXAMPLE 4

The reaction described in Example 1 was repeated on the same scale but with equivalent molar concentrations of 4-acetoxystyrene and allyl bromide. In this case, 4-allyloxystyrene was obtained in 69% yield following vacuum distillation.

EXAMPLE 5

The reaction described in Example 1 was repeated on the same scale but with the reaction temperature maintained in the range of 45° C., rather than 10° C., during the addition of 4-acetoxystyrene. Under these conditions the reaction exotherm could not be controlled and part of the reaction mixture was ejected from the reactor. After the exotherm had subsided, the procedure was continued and 4-allyloxystyrene was isolated in 66% yield. GC analysis showed this product contained 15% 4-vinylphenol as a side-product.

EXAMPLE 6

The reaction described in Example 1 was repeated on the same scale but with the reaction temperature maintained at ambient (23° C.), rather than 10° C., during the addition of 4-acetoxystyrene and allyl bromide. In this case, 4-allyloxystyrene was obtained in 66 % yield following vacuum distillation.

EXAMPLE 7

The reaction described in Example 4 was repeated on 0.04 scale but the water was omitted from the reaction mixture. In this case, 4-allyloxystyrene was obtained in 56% yield following vacuum distillation in a Kugelrohr distillation apparatus.

EXAMPLE 8

The reaction described in Example 1 was repeated on 0.04 scale but with 1 equivalent of potassium hydroxide. In this case GC analysis of the crude product showed only 50 % conversion of 4-acetoxystyrene to 4-allyloxystyrene in the mixture.

EXAMPLE 9

An aliquot (5.02 g) of the reaction product of Example 5 (4-allyloxystyrene containing 15 % 4-vinylphenol) was dissolved in 50 mls diethyl ether and the solution stirred with 50 ml of 1 molar potassium hydroxide solution for 3 hours. The mixture was poured into a separating funnel where it separated into 2 layers, a clear organic top layer and a yellow colored lower aqueous layer. The layers were separated and the organic fraction washed with three 50 ml portions of water, which removed residual hydroxide as indicated with a pH indicator strip analysis of the last aqueous extract. The washed organic portion was dried over anhydrous sodium sulfate, filtered and the solvent removed under reduced pressure to yield 2.88 g (58%) of 4-allyloxystyrene which was shown by GC analysis to have a concentration of 0.04% 4-vinylphenol.

EXAMPLE 10

An ultraviolet (UV) light sensitive composition was prepared by blending together the following materials: 4-allyloxystyrene (from Example 1) 50.0 g 2,2-bis-(3-allyl-4-vinyloxyethoxyphenyl)propane 16.7 g Cryacure UVI6974 (cationic photocatalyst supplied by Union Carbide) 1.4 g.

The blended composition is a low viscosity clear liquid. A drop of the composition was placed between two microscope slides and exposed to UV light from an Oriel 87331 projection lamp equipped with a 500 W mercury arc light. The incident intensity was measured with an IL 1700 photometer and diode detector and found to be 25 mW/cm$^2$ at 365 nm. After 20 seconds exposure the slides could not be separated without breaking the glass substrates, indicating good adhesion to glass.

EXAMPLE 11

A thin film of the liquid composition of Example 10 was spread onto a microscope slide and exposed to UV light for 60 seconds under the conditions described in example 10. The film, which had cured tack-free, was removed from the slide by means of a steel blade. A portion of the film was heated in a furnace at 315° C. for 1 hour, during which time a dark red/black color developed. Thermogravimetric analyses (TGA) were performed on both films. The film which was not heated at 315° C. showed an onset of degradation at 433° C. and a weight loss of 6% at that temperature. The film which was thermally treated following the UV exposure showed an onset temperature of 430° C. with a corresponding weight loss of 3% at that temperature. These results confirm the expected high temperature resistant properties of 4-allyloxystyrene derived adhesives and coatings.

EXAMPLE 12 SYNTHESIS OF 4-METHALLYLOXYSTYRENE

To a 4-necked, nitrogen swept, 2 liter glass reaction vessel equipped with a mechanical stirrer, double-walled condenser, thermometer and pressure compensating addition funnel was added tetrahydrofuran (THF) (600 mls), potassium hydroxide (112.0 g, 2.00 moles) and water (39 g). The mixture was stirred and cooled to 10° C. by means of an external ice-bath. 4-Acetoxystyrene (162.0 g, 1.00 moles) was added over a 5 minute period, during which time the temperature of the mixture increased to 40° C. The mixture was stirred for a further 1.5 hour during which time the temperature fell to 5° C. A solution of 3-chloro-2-methylpropene (methallyl chloride, 99.61 g, 1.10 moles) in THF (50mls) was added dropwise over 15 minutes and the reaction mixture stirred for a further 1.5 hours, throughout which time the temperature was maintained at 5°–10° C. The ice-bath was removed and the reaction mixture was slowly heated over 35 min. until the temperature reached 60° C. Heating and stirring were continued at this temperature for a further 2.5 hours. On cooling to ambient temperature, the mixture was filtered and the solvent removed from the filtrate under reduced pressure. The residue obtained was dissolved in toluene (300 mls) and the solution washed with four 300 ml portions of water. The organic fraction was dried over sodium sulfate, filtered, stripped of solvent under reduced pressure and combined to give a red colored liquid containing a small amount of a brown solid precipitate. The liquid was decanted from the solid residue to yield the crude reaction product (60.1 g). The liquid was distilled under vacuum to give a low melting crystalline solid (23.39 g) (b.p. 64°–72° C. at 0.2 torr) and a colorless liquid (14.08 g) (b.p.72°–74° C. at 0.2 torr). Spectroscopic analysis showed the crystalline solid to be 4-vinylphenol and the liquid to be the required monomer, 4-methallyoxystyrene (yield 16%).

EXAMPLE 13 SYNTHESIS OF 4-CROTYLOXYSTYRENE

To a 4-necked, nitrogen swept, 2 liter glass reaction vessel equipped with a mechanical stirrer, double-walled condenser, thermometer and pressure compensating addition funnel was added tetrahydrofuran (THF) (600 mls), potassium hydroxide (112.0 g, 2.00 moles) and water (39 g). The mixture was stirred and cooled to 6° C. by means of an external ice-bath. 4-Acetoxystyrene (162.0 g, 1.00 moles) was added over a 5 minute period, during which time the temperature of the mixture increased to 36° C. The mixture was stirred for a further 1 hour during which time the temperature fell to 10° C. A solution of crotyl chloride (99.61 g, 1.10 moles) in THF (50 mls) was added dropwise over 15 minutes and the reaction mixture stirred for a further 1 hour, throughout which time the temperature was maintained at 5°–10° C. The ice-bath was removed and the reaction mixture was heated slowly using a heating mantle. As the temperature approached 60° C., an exotherm was observed and the mixture began to reflux (67° C.). The heating mantle was removed and replaced with an ice-bath to control the exotherm. When the temperature had subsided to 57° C., the ice-bath was replaced with the heating mantle and the heating continued at 60° C. for a further 3 hours. On cooling to ambient temperature, the mixture was filtered and the solvent removed from the filtrate under reduced pressure. The residue obtained was dissolved in toluene (400 mls) and the solution washed with two 350 ml portions of water. The organic fraction was dried over sodium sulfate, filtered and the solvent removed under reduced pressure to give a red colored liquid (145.0 g). The liquid was dissolved in diethyl ether (200 ml) and extracted with three 200 ml portions 1M potassium hydroxide and followed by several portions of water, until the pH of the aqueous extract was neutral. The ether solution was dried over sodium sulfate, filtered and the solvent removed under reduced pressure to yield a yellow oil (57.34 g). Vacuum distillation of the crude oil afforded 4-crotyloxystyrene (42.11 g, 24%), b.p. 74°–83° C. at 0.6 torr.

EXAMPLE 14 SYNTHESIS OF 1,4-BIS(4'-VINYLPHENOXY)BUT-2-ENE

To a 500 ml 3-necked flask equipped with a thermometer, condenser and nitrogen inlet/addition funnel is added THF (170 ml), potassium hydroxide (13.81 g, 0.25 moles), and water (5 ml). The mixture is stirred by means of a magnetic stirrer and cooled to 12° C. by means of an external ice-bath. 4-Acetoxystyrene (20.2 g, 0.123 moles) is added dropwise over 7 minutes and the mixture stirred and cooled for a further 30 minutes. 1,4-Dibromo-2-butene (13.16 g, 0.062 moles) is added dropwise over 15 minutes and the mixture is allowed to warm to room temperature and then heated at 60° C. for 3 hours. After cooling to room temperature, the mixture is filtered and the THF solvent removed under reduced pressure. The residue is taken up in toluene (90 ml), refiltered and washed with 3×100 ml portions of water. The toluene solution is dried over sodium sulfate, filtered and the solvent removed to yield 13.48 g (37% yield) of a pale yellow colored solid, which is identified by spectroscopic analysis to be the required monomer, 1,4-bis(4'-vinylphenoxy)but-2-ene.

EXAMPLE 15 PREPARATION OF 4-ALLYLOXYSTYRENE USING 1,4-DIOXANE AS SOLVENT

To a 4-necked, nitrogen swept, 2 liter glass reaction vessel equipped with a mechanical stirrer, double-walled condenser, thermocouple and pressure compensating addition funnel is added 1,4-dioxane (600 mls), potassium hydroxide (112.0 g, 2.00 moles) and water (39 g). The mixture is stirred and cooled to 10° C. at which time 4-acetoxystyrene (162.0 g, 1.00 moles) is added over approximately 5 minutes. The mixture is stirred for a further 1.5 hour and cooled to 5° C. A solution of allylbromide (133.1 g, 1.10 moles) in 1,4-dioxane (50 mls) is added dropwise over 15 minutes and the reaction mixture is stirred for a further 1.5 hours, while the temperature is maintained between 5° and 10° C. The stirred mixture is gradually heated to 60° C. Heating and stirring are continued at this temperature for a further 2.5 hours. On cooling the mixture is filtered and most of the solvent is removed under reduced pressure. The residue obtained is dissolved in toluene (300 mls) and the solution washed with 4×300 ml portions of water, dried over sodium sulfate and the solvent distilled under reduced pressure to yield crude 4-allyloxystyrene in high yield.

EXAMPLE 16 PREPARATION OF 4-ALLYLOXYSTYRENE USING DIETHOXYMETHANE AS SOLVENT

A high yield of 4-allyloxystyrene is also obtained if diethoxymethane, rather than 1,4-dioxane, is used as the solvent in the reaction described in Example 15.

EXAMPLE 17 PREPARATION OF 4-ALLYLOXYSTYRENE USING 1,2-DIMETHOXYETHANE AS SOLVENT

A high yield of 4-allyloxystyrene is also obtained if 1,2-dimethoxyethane, rather than 1,4-dioxane, is used as the solvent in the reaction described in Example 15.

EXAMPLE 18 PREPARATION OF 4-METHALLYLOXYSTYRENE USING i,1-DIMETHOXYETHANE AS SOLVENT

A moderate yield of 4-methallyloxystyrene is obtained if methallyl chloride (1.1 moles) is used as the alkylating agent rather than allylbromide and 1,1-dimethoxyethane, rather than 1,4-dioxane, is used as the solvent in the reaction described in Example 15.

What is claimed is:

1. A method for the synthesis of allylic styrene ether compounds of the formula:

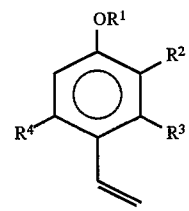

where $R^1$ is an, optionally substituted, allylic or propargyl hydrocarbon group, and $R^2$, $R^3$, and $R^4$ are independently H, $C_{1-6}$ hydrocarbon or $C_6$ hydrocarbonoxy groups, the method comprising reacting a 4-acyloxystyrene of the formula

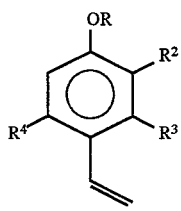

where R is an acyl group, with at least one mole of a base, which can readily saponify or hydrolyze the phenolic ester bond, per mole of acyloxystyrene, and then adding to the reaction mixture an alkylating agent of the formula $R^1X$, where $R^1$ is as previously defined and X is chloride, bromide, iodide, a sulfonic ester or a hydrocarbon sulfate group, to form said allylic styrene ether compound.

2. A method as in claim 1 wherein said base is an alkali hydroxide, alkali metal alkoxide or alkali metal hydrocarbon.

3. A method as in claim 2 wherein said base is an alkali hydroxide.

4. A method as in claim 2 wherein said base is selected from the group consisting of lithium hydroxide, lithium methoxide, lithium ethoxide, n-butyl lithium, potassium hydroxide, potassium methoxide, potassium ethoxide, sodium hydroxide, sodium methoxide and sodium ethoxide.

5. A method as in claim 1 wherein the groups $R^2$, $R^3$ and $R^4$ are H.

6. A method as in claim 1 wherein said base is employed in the reaction at a level of at least 1.5 equivalents per equivalent of acyloxystyrene.

7. A method as in claim 6 wherein said base is employed in the reaction at a level of at least 1.75 equivalents per equivalent of acyloxystyrene.

8. A method as in claim 7 wherein said base is employed at a level of about 2 equivalents of base per equivalent of acyloxystyrene.

9. A method as in claim 1 wherein R is a substituted or unsubstituted aromatic acyl group, or a substituted or unsubstituted alkyl acyl group.

10. A method as in claim 9 wherein the acyl group R is substituted with halogen, or alkoxy groups.

11. A method as in claim 1 wherein R is benzoate, toluate, acetate, propionate, butyrate, laurate, trimethylacetate, isobutyrate, trifluoroacetate, trichloroacetate, methoxybenzoate or chlorobenzoate.

12. A method as in claim 1 wherein $R^1$ is substituted with alkyl, aryl, halo, or hydrocarbonoxy groups.

13. A method as in claim 1 wherein $R^1$ is substituted with at least one member of the group consisting of methyl, ethyl, phenyl, tolyl, chloro, bromo and methoxy groups.

14. A method as in claim 1 wherein $R^1X$ is allyl chloride, allyl bromide, allyl iodide, methallyl chloride, methallyl bromide, methallyl iodide, 3-chloro-1-butene, crotyl chloride, crotyl bromide, crotyl iodide, propargyl chloride, propargyl bromide, propargyl iodide, cinnamyl chloride, cinnamyl bromide, cinnamyl iodide, 3-phenyl-3-bromo-1-propene, 2-phenyl-3-bromo-1-propene or 1,4-dibromo-2-butene, 2-phenyl-3-bromo-1-propene, allyl methyl sulfate, methallyl methyl sulfate, allyl tosylate, methallyl tosylate, crotyl tosylate, cinnamyl tosylate or allyl triflate.

15. A method as in claim 1 wherein $R^1X$ has two allylic chloride, bromide or iodide groups per molecule.

16. A method as in claim 1 wherein at least one of $R^2$, $R^3$ and $R^4$ is alkyl, alkenyl or alkoxy.

17. A method as in claim 16 wherein at least one of $R^2$, $R^3$ and $R^4$ is methyl, ethyl, vinyl, methoxy or ethoxy.

18. A method as in claim 1 wherein said reaction mixture includes a solvent system comprising an ether solvent.

19. A method as in claim 18 wherein said ether solvent is a linear or cyclic aliphatic ether in which water is soluble at a level of at least 5% by weight and which has a boiling point in the range of from about 40° C. to about 130° C.

20. A method as in claim 18 wherein said ether solvent is selected from the group consisting of tetrahydrofuran, tetrahydropyran, 1,4-dioxane, 1,3-dioxane, dimethoxymethane, diethoxymethane, 1,1-dimethoxyethane, 1,1-diethoxyethane, 1,2-dimethoxyethane and 1,2-diethoxyethane.

21. A method as in claim 18 wherein the solvent system further comprises water in an amount of at least 5% of said solvent system.

22. A method as in claim 1 wherein in said reacting step, said 4-acyloxystyrene has an initial concentration of at least 1 mole per liter of said solvent.

23. A method as in claim 1 wherein said ether has a boiling point at ambient pressure of from about 50° C. to about 120° C.

24. A method as in claim 18 further comprising separating the allylic styrene ether product from the remaining constituents of the reaction mixture, said separating step comprising filtering the reaction mixture to remove solids, evaporating the solvent in the filtrate and extracting the residue of the evaporation with a two-phase system of water and a water-insoluble organic extraction solvent to isolate said allylic styrene ether in said water-insoluble organic extraction solvent.

25. A method as in claim 1 wherein X is tosylate, triflate, methyl sulfate or ethyl sulfate.

26. A method as in claim 1 wherein X is Cl, Br or I.

27. The compound 1,4-bis(4'-vinylphenoxy)but-2-ene.

* * * * *